(12) United States Patent
Hissong

(10) Patent No.: US 9,610,069 B2
(45) Date of Patent: Apr. 4, 2017

(54) TISSUE STABILIZATION AND REPAIR DEVICE

(71) Applicant: Medtronic-Xomed, Inc., Jacksonville, FL (US)

(72) Inventor: James B. Hissong, Jacksonville, FL (US)

(73) Assignee: Medtronic-Xomed, Inc., Jacksonville, FL (US)

( * ) Notice: Subject to any disclaimer, the term of this patent is extended or adjusted under 35 U.S.C. 154(b) by 152 days.

(21) Appl. No.: 13/871,826

(22) Filed: Apr. 26, 2013

(65) Prior Publication Data

US 2014/0324098 A1    Oct. 30, 2014

(51) Int. Cl.
*A61B 17/00* (2006.01)
*A61B 17/11* (2006.01)

(52) U.S. Cl.
CPC . *A61B 17/00491* (2013.01); *A61B 2017/1103* (2013.01)

(58) Field of Classification Search
CPC ...... A61B 17/00491; A61B 2017/1103; A61B 17/11; A61B 2017/00495; A61B 2017/005; A61B 2017/00513; A61B 2017/00522; A61B 2017/081; A61B 17/08; A61B 17/085; A61B 17/3401; A61B 2017/3403; A61B 2017/3407; A61M 5/3216; A61M 25/0612; A61M 25/0631; A61M 25/0618; A61M 5/3202; A61M 5/46; A61M 25/0637
USPC .................. 606/213, 214, 215; 604/115–117
See application file for complete search history.

(56) References Cited

U.S. PATENT DOCUMENTS

| | | | |
|---|---|---|---|
| 3,943,628 A | | 3/1976 | Kronman et al. |
| 5,108,403 A | | 4/1992 | Stern |
| 5,681,333 A | * | 10/1997 | Burkhart et al. ............. 606/148 |
| 5,759,194 A | * | 6/1998 | Hammerslag ................. 606/214 |
| 5,984,950 A | * | 11/1999 | Cragg et al. .................... 606/216 |
| 6,033,427 A | * | 3/2000 | Lee ................. 606/213 |
| 6,245,080 B1 | * | 6/2001 | Levinson ...................... 606/144 |
| 6,328,743 B2 | * | 12/2001 | Lerch ............................. 606/324 |
| 8,277,458 B2 | * | 10/2012 | Schneider ........................ 606/96 |
| 8,858,593 B2 | * | 10/2014 | Kerber .......................... 606/213 |
| 2004/0215231 A1 | * | 10/2004 | Fortune .............. A61B 17/0057 606/213 |
| 2006/0009801 A1 | * | 1/2006 | McGurk et al. .............. 606/214 |

(Continued)

FOREIGN PATENT DOCUMENTS

WO      03022457 A1    3/2003

OTHER PUBLICATIONS

Synonym: Deflect; NPL_deflect_synonym.pdf; http://www.thesaurus.com/browse/deflect; Jan. 4, 2015.*

(Continued)

*Primary Examiner* — Tuan V Nguyen
*Assistant Examiner* — Chima Igboko
(74) *Attorney, Agent, or Firm* — Dicke, Billig & Czaja, PLLC

(57) ABSTRACT

A device includes an elongated cannula with an opening positioned at its distal end. A tissue engagement structure is affixed proximate the distal end of the cannula and surrounds the opening. The tissue engagement structure includes a tissue engaging portion to engage and control tissue. An adhesive is dispensed through the cannula opening to repair tissue.

9 Claims, 4 Drawing Sheets

(56) References Cited

U.S. PATENT DOCUMENTS

| | | | |
|---|---|---|---|
| 2009/0069846 A1* | 3/2009 | Bull | A61B 17/0469 606/228 |
| 2009/0299375 A1* | 12/2009 | Wack et al. | 606/96 |
| 2009/0299406 A1* | 12/2009 | Swain et al. | 606/215 |
| 2010/0191247 A1* | 7/2010 | Schneider | 606/96 |
| 2010/0262183 A1* | 10/2010 | Abbott | A61B 17/0057 606/213 |
| 2011/0082497 A1* | 4/2011 | Deslauriers et al. | 606/213 |
| 2011/0144419 A1* | 6/2011 | Timm | A61F 5/0056 600/37 |
| 2012/0046691 A1* | 2/2012 | Belson et al. | 606/214 |
| 2012/0065674 A1* | 3/2012 | Levy | 606/214 |
| 2012/0083831 A1* | 4/2012 | Peterson | 606/213 |
| 2012/0143246 A1* | 6/2012 | Zhu et al. | 606/215 |
| 2013/0211450 A1* | 8/2013 | Whitman | 606/215 |
| 2013/0245680 A1* | 9/2013 | Sargeant et al. | 606/214 |
| 2014/0142618 A1* | 5/2014 | Leopold et al. | 606/213 |

OTHER PUBLICATIONS

PCT Search Report and Written Opinion for PCT/US2014/035485, mailed Sep. 1, 2014, 11 pages.

* cited by examiner

TISSUE STABILIZATION AND REPAIR DEVICE

BACKGROUND

Following surgery on an internal structure of the body, a surgeon utilizes sutures or other mechanisms to assist in healing the internal structure properly. For example, during septal surgery, a surgeon dissects a portion of the septal lining during the procedure. Once the surgery is complete, the surgeon folds back the septal lining to its original location. In order to heal properly, the surgeon applies a suture to the septal lining and septum in order for the septal lining to heal in place. Attaching a suture within an interior cavity of the patient can be difficult using current approaches, as a surgeon handles both an endoscope and tools to install the suture.

SUMMARY

A method of stabilizing and repairing tissue includes providing a device having a tissue engagement structure surrounding an opening of an elongated cannula. The cannula extends from a proximal end to a distal end and defines a lumen. The device is positioned within a cavity that includes a first tissue structure and a second tissue structure at least partially separated from the first tissue structure. A free end of the second tissue structure is gripped with the tissue engagement structure. The second tissue structure is moved toward the first tissue structure using the tissue engagement structure. An adhesive is dispensed through the opening to the first tissue structure and the second tissue structure.

A device includes an elongated cannula with an opening positioned at its distal end. A tissue engagement structure is affixed proximate the distal end of the cannula and extends distally beyond the opening. The tissue engagement structure includes a gripping structure to engage and control tissue. An adhesive is dispensed through the opening of the cannula to repair tissue.

DETAILED DESCRIPTION

Figure 1:
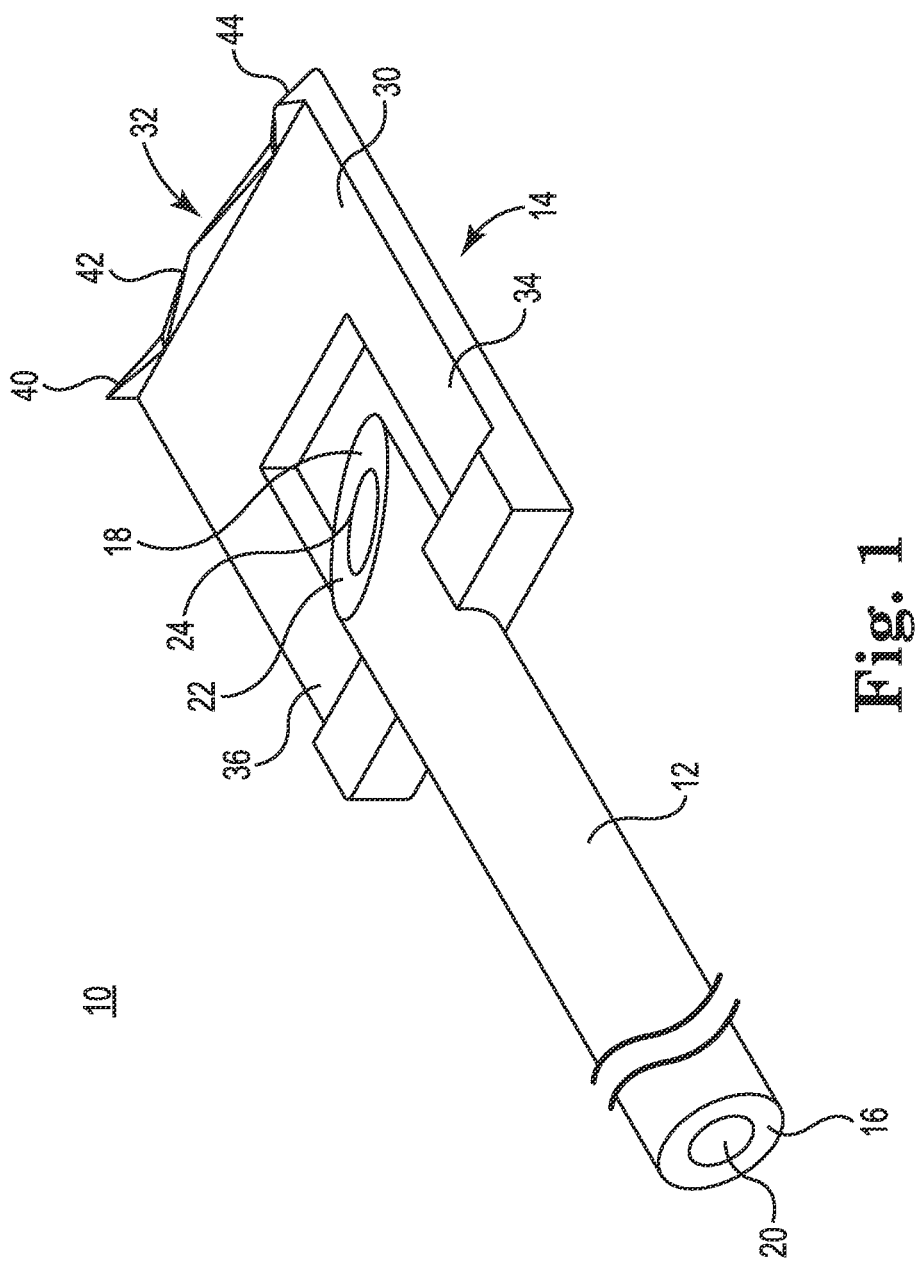
FIGS. 1 and 2 are isometric views of a tissue stabilization and repair device.
Figure 2:
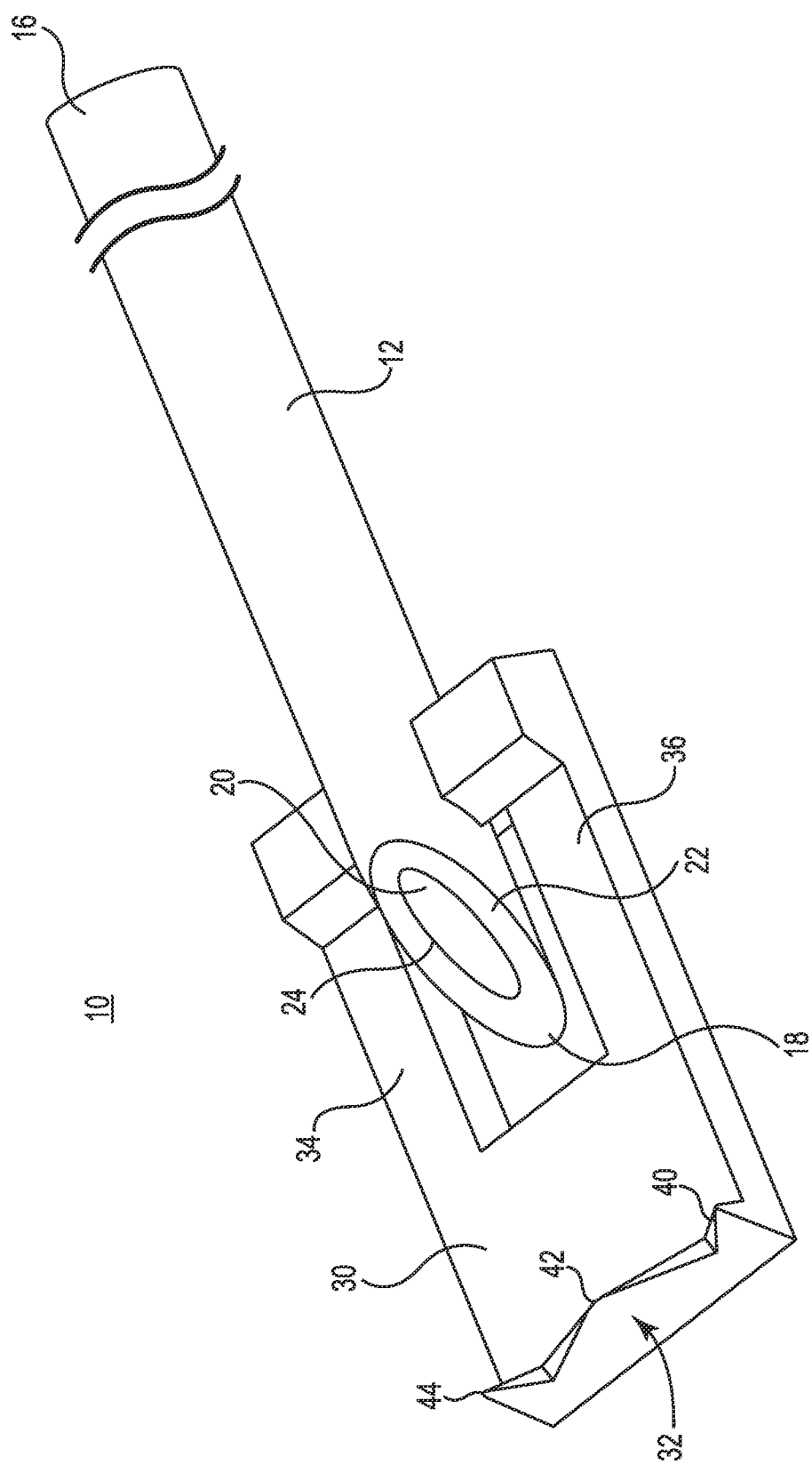

FIGS. 1 and 2 illustrate an isometric view of a tissue stabilization and repair device 10 that includes an elongated cannula 12 and a tissue engagement structure 14. The cannula 12 extends from a first, proximal end 16 to a second, distal end 18. The cannula 12 defines an interior lumen 20 extending along the cannula 12 from the proximal end 16 to the distal end 18. Distal end 18 includes a beveled tip 22 defining an elongated opening 24. During use, an adhesive (e.g., cyanoacrylate or other fast curing adhesive) is positioned within lumen 20 at the proximal end 16. The adhesive is then delivered through the lumen 20 to the opening 24. The proximal end 16 can be configured to receive the adhesive from a suitable adhesive dispenser. For example, the dispenser can be a syringe with a plunger that is connectable to proximal end 16, wherein the plunger is used to move the adhesive along the lumen 20 to opening 24. In another example, the dispenser can be a tube filled with adhesive that is connected to proximal end 16 and squeezed to move the adhesive along lumen 20 to opening 24 or the tip end 16 can be integral with the adhesive container.

Engagement structure 14 assists in stabilizing tissue to be repaired. In particular, the engagement structure 14 extends distally beyond the distal end 18 of the cannula 12 and includes a base portion 30, a distal tissue engagement portion 32 and opposed legs 34 and 36 extending from the base portion 30 and positioned on one or either side of cannula 12. Base portion 30 is generally planar and configured to engage and stabilize a portion of tissue while adhesive is applied through opening 24 to a portion of tissue to be repaired. Legs 34 and 36 are coupled to cannula 12 and, in one embodiment, allow for relative movement between the tissue engagement portion 32 and cannula 12. For example, the legs 34 and 36 can be formed with sufficient flexibility to deflect with respect to the tissue engagement portion 32 such that cannula 12 rotates with respect to the tissue engagement portion 32 when a force is applied to the tissue engagement portion 32. In another example, cannula 12 can be rotatably coupled to legs 34 and 36 to rotate relative thereto when a force is applied to tissue engagement portion 32.

Tissue engaging portion 32 includes one or more teeth extending from the base portion 30 and is positioned spaced apart from the distal end 18 and opening 24 of cannula 12. In particular, the base portion 30 is positioned between the opening 24 and the distal engagement portion 32, the distal engagement portion 32 positioned at an end of the base portion 30 opposite the proximal end 16 of the cannula 12. The distal engagement portion 32 can extend from base portion 30 at various angles, for example, at least 45 degrees, at least 60 degrees, at least 90 degrees, greater than 90 degrees, etc. Illustratively, distal engagement portion 32 includes a first tooth 40, a second tooth 42 and a third tooth 44. The second tooth 42 is positioned between the first tooth 40 and third tooth 44 and is illustrated as having a larger surface area than either tooth 40 or tooth 44. It will be appreciated that any number of teeth (e.g., at least one, three, five) can be provided that extend from the base portion to assist in engaging tissue. Additionally, the teeth can be different sizes as desired.

Figure 3:
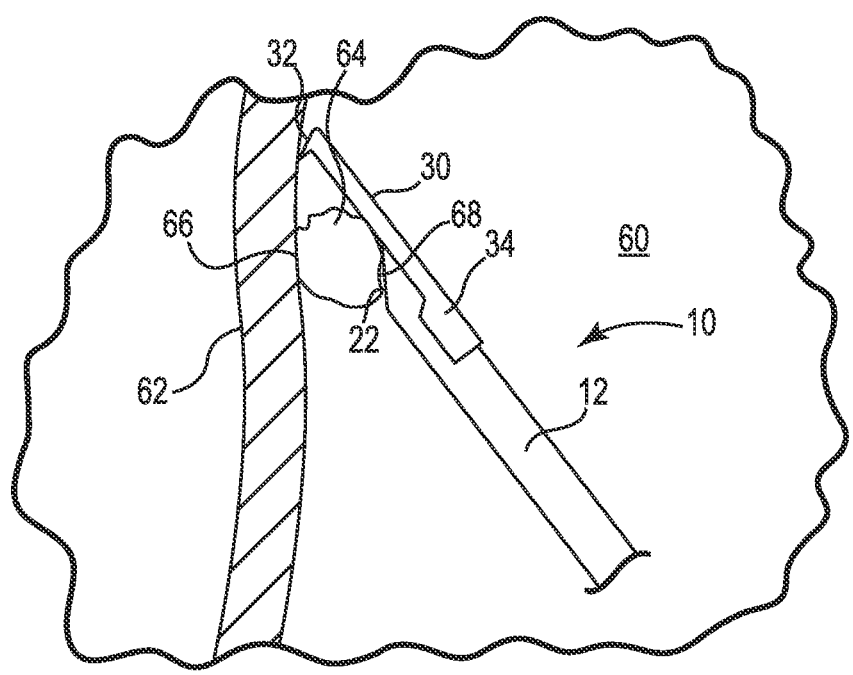
FIG. 3 is a schematic diagram of the device of FIG. 1 gripping a portion of tissue.
Figure 4:
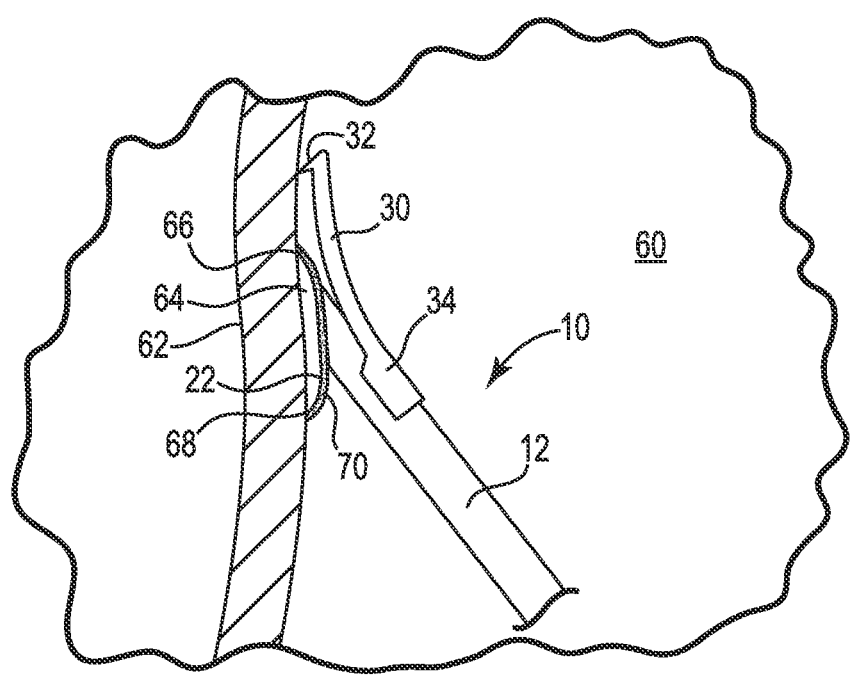
FIG. 4 is a schematic diagram of the device of FIG. 1 stabilizing and repairing a portion of tissue.

As illustrated in FIGS. 3 and 4, during a method of tissue stabilization and repair, device 10 is inserted into a cavity 60 (e.g., a sinus cavity) including a first tissue structure 62 (e.g., a septal wall) and a second tissue structure 64 (e.g., a septal lining) at least partially separated from the first tissue structure 62. In the embodiment illustrated, the second tissue structure 64 is fixed to the first tissue structure 62 at a first end 66 and free from the first tissue structure 62 at a second end 68. To repair separation of the second tissue structure 64 from the first tissue structure 62, the distal engagement portion 32 engages the second tissue structure 64 (e.g., at the second end 68) and moves the second tissue structure 64 to engage the first tissue structure 62. In particular, second end 68 is brought into contact or in close proximity to the first tissue structure 62 as illustrated in FIG. 4.

Once device 10 has positioned second tissue structure 64 into place, a force (i.e., pressure, indicated by arrow P) can be applied to device 10 to push second tissue structure 64 against first tissue structure 62. In one embodiment, the pressure causes cannula 12 to flex with respect to tissue engagement portion 32. For example, the pressure can cause legs 34 and 36, along with distal end 18 of cannula 12, to rotate with respect to the tissue engagement portion 32.

Alternatively, or in addition to, distal end 18 can be rotatably coupled to legs 34 and 36 to facilitate flexing of the cannula 12 with respect to the tissue engagement portion 32. In one embodiment, flexing of the cannula 12 rotates beveled tip 22 such that the beveled tip 22 is orientated substantially parallel to the first tissue structure 62. Regardless of the orientation of beveled tip 22 with respect to the first tissue structure 62, an adhesive 70 can be dispensed through opening 24. The adhesive 70 is dispensed to adhere the second tissue structure 64 to the first tissue structure 62. After the adhesive 70 is dispensed, device 10 can be removed from cavity 60, allowing the adhesive 70 to cure in order to adhere the second tissue structure 64 to the first tissue structure 62. Alternatively, the pressure to first tissue structure 62 can be applied while adhesive 70 cures sufficiently to hold the first tissue structure 62 and second tissue structure 64 together.

Although the present disclosure has been described with reference to preferred embodiments, workers skilled in the art will recognize that changes can be made in form and detail without departing from the spirit and scope of the present disclosure.

What is claimed is:

1. A tissue stabilization and repair device, comprising:
   a single-piece elongated cannula extending from a proximal end to a beveled tip at a distal end and
   defining a lumen including an elongated opening at the distal end; and
   a tissue engagement structure extending distally beyond the opening and including a base portion located distal the distal end of the cannula, a tissue engaging portion extending from the base portion, and two opposing legs extending from the base portion, wherein the two opposing legs are directly affixed to the cannula proximate the distal end, and further wherein the opening is positioned between the legs;
   wherein the device is configured such that a point of attachment of the legs with the cannula is longitudinally fixed relative to the beveled tip.

2. The device of claim 1, wherein the tissue engaging portion includes a plurality of teeth.

3. The device of claim 1, wherein the tissue engaging portion deflects relative to the distal end of the cannula upon a force being applied to the tissue engaging portion.

4. The device of claim 1, further comprising an adhesive positioned within the lumen.

5. The device of claim 1, wherein the base portion is substantially planar and is positioned between the opening and the tissue engaging portion.

6. The device of claim 1, wherein the legs can flex relative to the tissue engaging portion.

7. The device of claim 1, wherein the cannula is rotatably coupled to the legs.

8. The device of claim 1, wherein the device is configured to be inserted within a sinus cavity.

9. The device of claim 1, wherein the base portion terminates at opposing, leading and trailing ends, and further wherein the leading end defines a most-distal edge of the base portion, and even further wherein the leading end and the trailing end are both distally spaced from the distal end of the cannula.

* * * * *